United States Patent
Woestenborghs

(10) Patent No.: US 9,708,239 B2
(45) Date of Patent: Jul. 18, 2017

(54) PROCESS FOR THE SEPARATION OF LEVULINIC ACID FROM A BIOMASS HYDROLYSATE

(71) Applicant: Georgia-Pacific LLC, Atlanta, GA (US)

(72) Inventor: Pierre Louis Woestenborghs, Echt (NL)

(73) Assignee: Georgia-Pacific LLC, Atlanta, GA (US)

( * ) Notice: Subject to any disclaimer, the term of this patent is extended or adjusted under 35 U.S.C. 154(b) by 0 days.

(21) Appl. No.: 14/786,776

(22) PCT Filed: Apr. 24, 2014

(86) PCT No.: PCT/EP2014/058305
§ 371 (c)(1),
(2) Date: Oct. 23, 2015

(87) PCT Pub. No.: WO2014/173995
PCT Pub. Date: Oct. 30, 2014

(65) Prior Publication Data
US 2016/0152542 A1    Jun. 2, 2016

(30) Foreign Application Priority Data

Apr. 25, 2013 (EP) ..................... 13165383
Oct. 11, 2013 (EP) ..................... 13188264
Jan. 2, 2014 (EP) ..................... 14150068

(51) Int. Cl.
C07C 51/47 (2006.01)
C07C 51/48 (2006.01)
(Continued)

(52) U.S. Cl.
CPC ............. *C07C 51/47* (2013.01); *C07C 39/06* (2013.01); *C07C 39/07* (2013.01); *C07C 39/08* (2013.01);
(Continued)

(58) Field of Classification Search
None
See application file for complete search history.

(56) References Cited

U.S. PATENT DOCUMENTS

2014/0018555 A1* 1/2014 De Vries ................. C07C 51/00
549/489
2014/0128634 A1* 5/2014 Mullen .................. C07C 51/00
562/577

FOREIGN PATENT DOCUMENTS

CN    102090449 B    5/2013
EP    0575010 A1    12/1992
(Continued)

OTHER PUBLICATIONS

Knight, G.W., et a., The estimation of phenol in the presence of the three cresols, 1918, The Journal of Industrial and Engineering Chemistry, vol. X, issue 1, pp. 10.*
(Continued)

*Primary Examiner* — Yate K Cutliff
(74) *Attorney, Agent, or Firm* — Ram W. Sabnis

(57) ABSTRACT

The invention provides a process to separate levulinic acid from a biomass hydrolysate said process comprising extraction using as an organic solvent a substituted benzene comprising (i) at least one $OR_1$ group wherein $R_1$ is H or $CH_3$; and (ii) at least one $C_{1-3}$ alkyl group, wherein each of the at least one $OR_1$ group is ortho positioned to at least one $C_{1-3}$ alkyl group. Using said substituted benzene as extraction solvent gives good extraction efficiency, the extraction
(Continued)

can advantageously be carried out at elevated temperature, and is very suitable for subsequent distillation steps.

20 Claims, 4 Drawing Sheets

(51) Int. Cl.
C07C 39/06 (2006.01)
C07C 39/07 (2006.01)
C07C 39/08 (2006.01)
C07C 43/295 (2006.01)
C07C 51/44 (2006.01)

(52) U.S. Cl.
CPC ............ C07C 43/295 (2013.01); C07C 51/44 (2013.01); C07C 51/48 (2013.01)

(56) References Cited

FOREIGN PATENT DOCUMENTS

| | | | |
|---|---|---|---|
| WO | 2010103126 A1 | 9/2010 | |
| WO | 2011043665 A1 | 4/2011 | |
| WO | WO 2012/162028 | * | 11/2012 |
| WO | 2014173995 A1 | 10/2014 | |

OTHER PUBLICATIONS

International Search Report from corresponding PCT/EP2014/058236, mailed Jul. 21, 2014.

Alonso et al., "Production of Biofuels from Cellulose and Corn Stover Using Alkylphenol Solvents", Wiley-VCH Verlag GmbH & Co. KGaA, Weinheim, ChemSusChem 2011, XP002712059, vol. 4, pp. 1078-1081.

Demirkaya et al., "The effect of microbial transglutaminase on microbiological, chemical, textural and sensory properties of yogurt", The Australian Journal of Dairy Technology, XP9170407A, vol. 64, No. 2, Oct. 2009, pp. 171-176.

Frank et al., "Liquid-Liquid Extraction and Other Liquid-Liquid Operations and Equipment", Perry's Chemical Engineers' Handbook, 8th Edition, Section 15, 2008, pp. 15-1 thru 15-105.

* cited by examiner

PROCESS FOR THE SEPARATION OF LEVULINIC ACID FROM A BIOMASS HYDROLYSATE

CROSS REFERENCE TO RELATED APPLICATIONS

This application is a §371 National Stage Application of PCT/EP2014/058305, filed 24 Apr. 2014, which claims priority to EP 13165383.4, filed 25 Apr. 2013, EP 13188264.9, filed 11 Oct. 2013 and EP 14150068.6, filed 2 Jan. 2014.

BACKGROUND

Field of the Invention

The present invention relates to a process to separate levulinic acid from a biomass hydrolysate using as an organic solvent a substituted benzene and to the use of such substituted benzenes in the separation of levulinic acid from a biomass hydrolysate.

Background of the Invention

Isolation of many industrial compounds involves the use of both extraction and distillation. Extraction takes advantage of differences in the chemical properties of the feed components, such as differences in polarity and hydrophobic/hydrophilic character to separate them (T. C. Frank, L. Dahuron, B. S. Holden, W. D. Prince, A. F. Seibert, L. C. Wilson, Liquid-liquid extraction and other liquid-liquid operations and equipment in Perry's Chemical Engineering Handbook, 8th Edition, Section 15). After a compound of interest has been extracted from an aqueous composition the valuable compound is usually further purified by subjecting the organic phase to distillation. A suitable extraction solvent must not only give good extraction efficiency, but must also be compatible with a distillation as a subsequent separation step. For example, a solvent must not form a complex with the target compound during distillation, or result in the formation of degradation or side products. In other words, a solvent which gives good extraction efficiency but results in the formation of side products in a distillation is not suitable. Likewise, a solvent which gives no problems during distillation but gives poor extraction efficiency is also not suitable.

SUMMARY

Levulinic acid is a starting molecule for the synthesis of esters known as fuel additive and is known to be useful as plasticizers and solvents. Levulinic acid can be used to synthesize methyl tetrahydrofuran (MTHF) or can be used as a solvent. Other applications of levulinic acid are for example the synthesis of delta-amino levulinic acid used as herbicides and pesticides, diphenolic acid used to synthesize polycarbonates and succinic acid used to make polyesters. Levulinic acid can also be used to produce gamma valerolactone (5-methylbutyrolactone), which in turn can be used for production of adipic acid (1,6-hexanedioic acid).

Levulinic acid can be produced from furfuryl alcohol. It is also possible to produce levulinic acid by acid hydrolysis of biomass although this is not commercially practiced. Alonso et al. (ChemSusChem 2011, vol 4, pp 1078-1081) describe isolation of levulinic acid with solvent extraction using 2-sec-butylphenol as solvent to extract levulinic acid.

A problem of 2-sec-butylphenol is that the extraction coefficient is insufficient. It is an aim to provide an improved separation process for levulinic acid from a biomass hydrolysate. It is another aim to provide a separation process for levulinic acid from a biomass hydrolysate comprising extraction which gives good extraction efficiency and which is suitable for use in a (subsequent) distillation step. It is another aim to provide a separation process for levulinic acid from a biomass hydrolysate comprising extraction which process can be carried out at around 60° C.

DETAILED DESCRIPTION OF A PREFERRED EMBODIMENT

Figure 1:
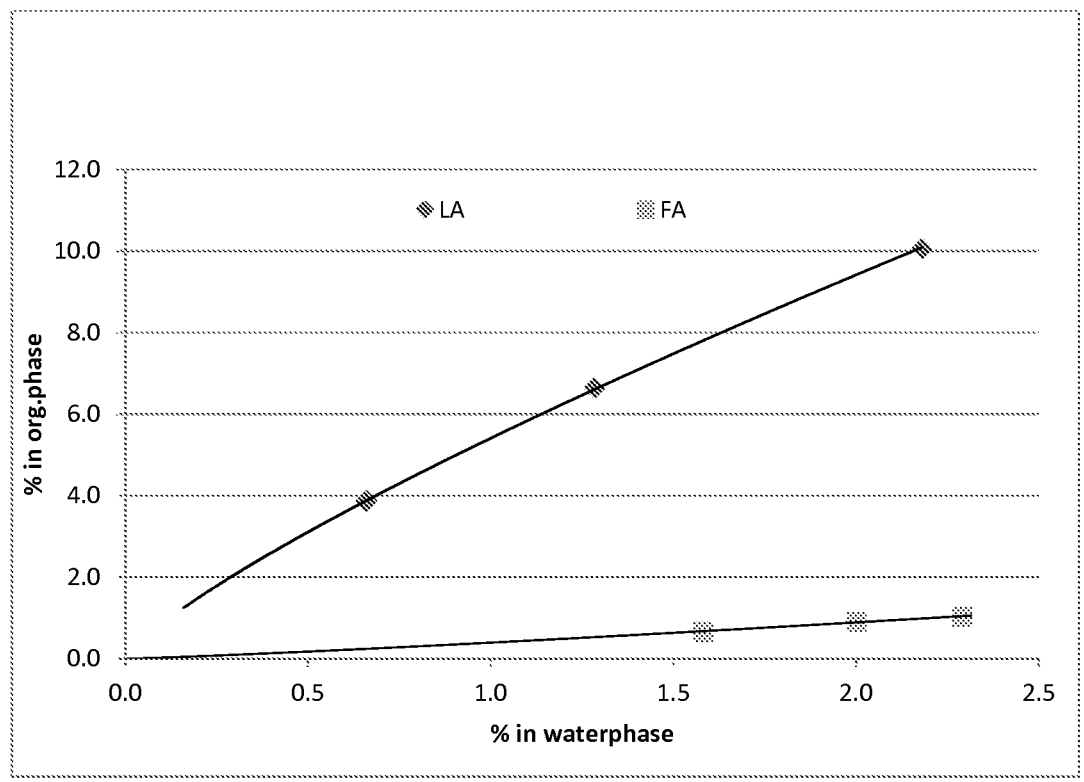
FIGS. 1-4 depict embodiments as described herein.
Figure 2:
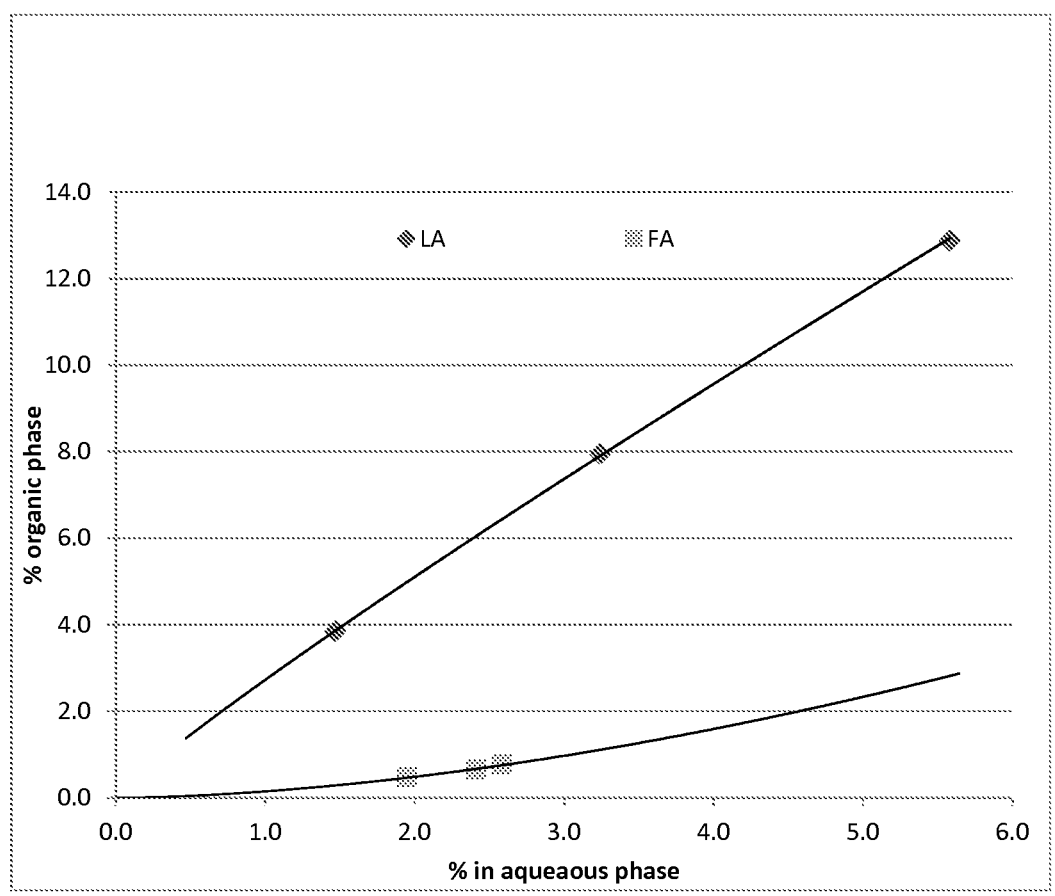
Figure 3:
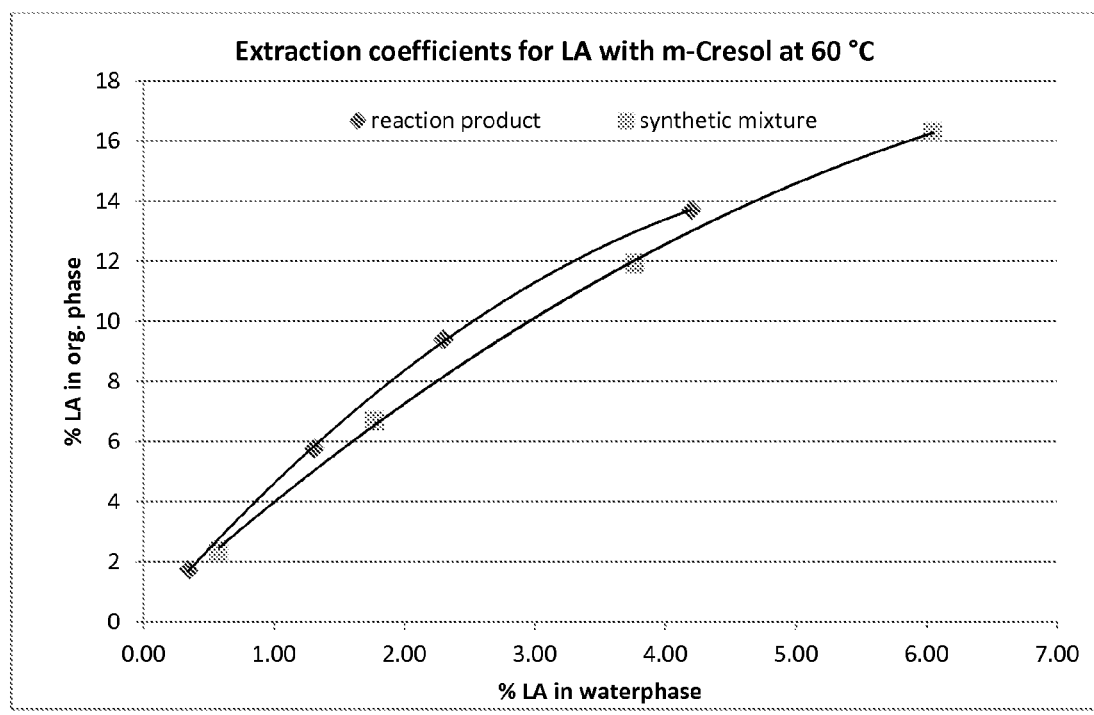
Figure 4:
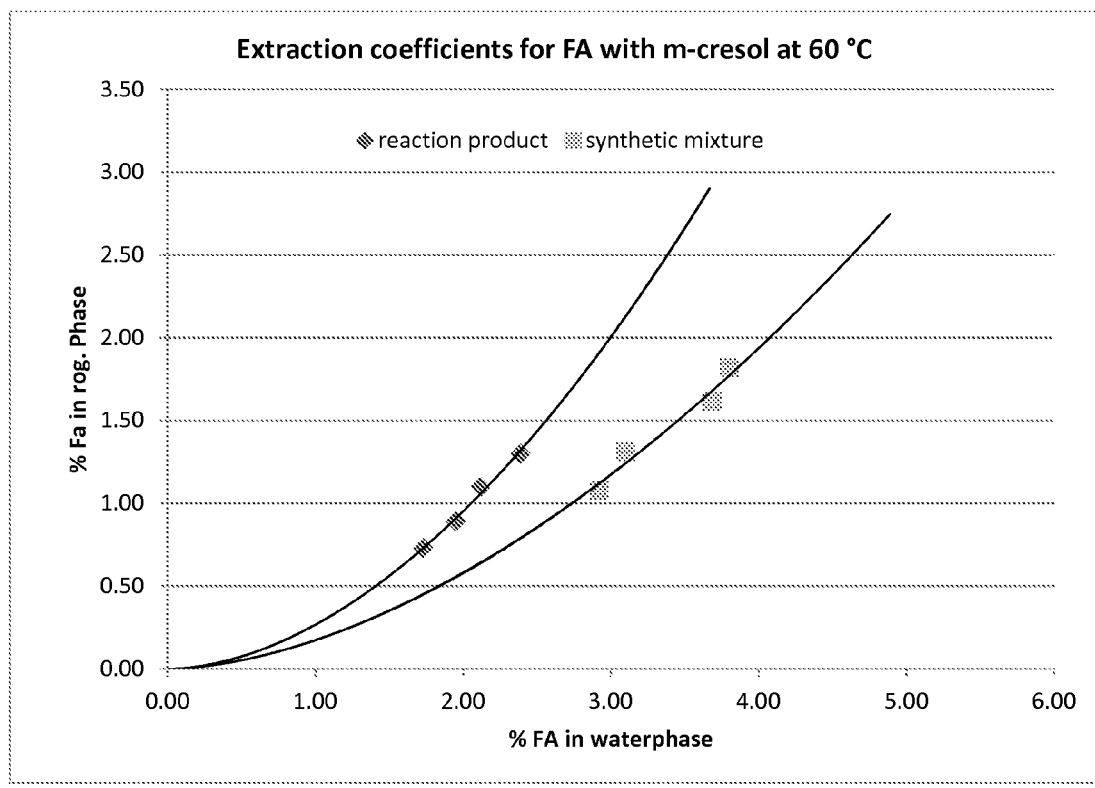

Therefore, in a first aspect, the invention relates to a process to separate levulinic acid from a biomass hydrolysate said process comprising extraction using as an organic solvent a substituted benzene comprising:
(i) at least one $OR_1$ group wherein $R_1$, is H or $CH_3$; and
(ii) at least one $C_{1-3}$ alkyl group,
wherein each of the at least one $OR_1$ group is ortho positioned to at least one $C_{1-3}$ alkyl group.

Throughout this invention, "the solvent" shall refer to a substituted benzene comprising: (i) at least one $OR_1$ group wherein $R_1$, is H or $CH_3$; and (ii) at least one $C_{1-3}$ alkyl group, and wherein each of the at least one $OR_1$ group is ortho positioned to at least one $C_{1-3}$ alkyl group. The solvent may be a mixture comprising the solvent and other solvents.

The inventor has found that by using the solvent in the extraction of levulinic acid, a surprisingly high extraction efficiency can be obtained, and formation of levulinic acid side products during a distillation step may be reduced. In contrast, if a substituted benzene is used which contains an $OR_1$ group which does not have a neighboring (ortho positioned) $C_{1-3}$ alkyl group, such as for example a phenol having a meta or para alkyl group and having no ortho $C_{1-3}$ group, side products of levulinic acid may be formed during distillation. Moreover, if a substituted benzene is used having an alkyl group having more than 3 C atoms, the extraction efficiency is lower than when such alkyl group contains 1, 2, or 3 atoms.

Any $OR_1$ group must have at least one neighboring (ortho positioned) $C_{1-3}$ alkyl group in the aryl ring. If the solvent comprises more than one $OR_1$ group, each of the $OR_1$ groups must have at least one $C_{1-3}$ alkyl group positioned ortho to said $OR_1$ group.

The at least one $OR_1$ group can have one or two ortho positioned $C_{1-3}$ alkyl groups. If the solvent comprises more than one $OR_1$ group, said $OR_1$ groups may be the same or different. By way of example, the solvent may have one hydroxyl group or one methoxy group; two, three, or more hydroxyl groups; two, three, or more methoxy groups; or a combination thereof such as for example one hydroxyl group and one methoxy group; two hydroxyl groups and one methoxy group; or one hydroxyl group and two methoxy groups.

The solvent is preferably selected from the group consisting of compounds I to VI:

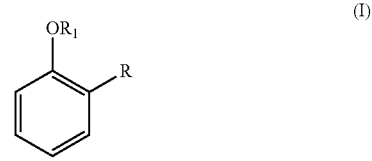

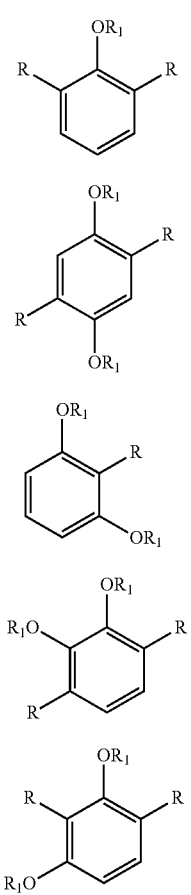

wherein R represents a $C_{1-3}$ alkyl group and $R_1$, is defined as above. The solvent may also be a mixture of two or more of compounds I through VI.

The number of $C_{1-3}$ alkyl groups is not necessarily the same as the number of $OR_1$ groups. For example, two $OR_1$ groups may share one ortho $C_{1-3}$ alkyl group as for example in compound IV, and one $OR_1$ group may have two ortho-positioned $C_{1-3}$ alkyl groups as for example in compound II.

The $C_{1-3}$ alkyl group may be methyl, ethyl, propyl or isopropyl. If the solvent comprises more than one $C_{1-3}$ alkyl group, said $C_{1-3}$ alkyl groups may be the same or different.

In an embodiment the at least one $C_{1-3}$ alkyl group is a methyl group. In another embodiment the solvent is ortho-cresol or 2,6 dimethyl phenol, or a mixture thereof.

In the context of the invention, "extraction", "solvent extraction", and "solvent-solvent extraction" are understood to be the same. Extraction is used to separate levulinic acid from a biomass hydrolysate. Extraction yields an aqueous phase and an organic phase. Extraction may be carried out such that the solvent is added to the biomass hydrolysate. Water, or other solvents which are immiscible with the solvent, may be added to the biomass hydrolysate prior to extraction.

Extraction is preferably carried out at elevated temperature, preferably at a temperature above 20° C., more preferably at a temperature ranging from 50 to 80° C., most preferably a temperature of about 60° C. At extraction temperatures above 80° C., the extraction efficiency may be too low. At extraction temperatures below 50° C., the process may require too much cooling water, in order to cool the biomass hydrolysate.

The process of the invention may include providing a biomass hydrolysate and subjecting said biomass hydrolysate to extraction. The biomass hydrolysate may be subjected to extraction as-is, e.g. as it leaves the hydrolysis reactor. Alternatively, the biomass hydrolysate may undergo one or more steps before extraction. The biomass hydrolysate may be subjected to extraction by adding the solvent, e.g. under stirring. The skilled person knows how to carry out extraction.

Typically, the aqueous phase contains 2-15 wt % mineral acid (usually $H_2SO_4$), which is derived from the biomass hydrolysate.

Optionally the organic phase comprising levulinic acid is recovered. The organic phase (comprising the solvent) can be recovered from the aqueous phase by methods known to the skilled person.

In an embodiment, prior to the extraction, the biomass hydrolysate is subjected to solid-liquid separation. This yields a liquid fraction and a solid fraction. The liquid fraction, which comprises levulinic acid, is recovered. Said recovered liquid fraction can be subjected to extraction.

Therefore, the invention includes a process to separate levulinic acid from a biomass hydrolysate comprising:
  optionally subjecting the biomass hydrolysate to a concentration step via flash evaporation;
  subjecting the optionally concentrated biomass hydrolysate to solid-liquid separation to yield a liquid fraction and a solid fraction and recovering the liquid fraction;
  subjecting the liquid fraction to extraction comprising an organic phase comprising the solvent, and an aqueous phase; and
  recovering the organic phase.

In an embodiment the recovered organic phase is subjected to distillation. This advantageously allows separation of the solvent from the levulinic acid, making use of the low boiling point of the solvent. The process may comprise one, two, or more distillations. In the context of the invention, the term "the distillation" does not necessarily mean that there is only one distillation. The use of the solvent in the extraction may prevent formation of side products during subsequent distillation, such as levulinic acid esters. The levulinic acid may be recovered as a distillate, or as a distillation residue. The solvent can be easily separated from the levulinic acid by recovering the solvent as a distillate, and the levulinic acid as the distillation residue. Any other compounds present in the residue, such as formic acid, may be separated by subsequent distillation, where levulinic acid can be recovered as a distillate.

The biomass may be or may be derived from wood, grass, cereal, starch, algae, tree bark, hay, straw, leaves, paper pulp, paper sludge, or dung. Paper pulp, or simply pulp, is a lignocellulosic fibrous material prepared by chemically or mechanically separating cellulose from wood, fibre crops or waste paper. Pulp is rich in cellulose and other carbohydrates. Paper sludge, or simply sludge, is a lignocellulosic fibrous containing cellulose fibres too short for usage in the paper industry. The biomass may comprise lignocellulosic biomass. Lignocellulosic biomass typically has a fibrous nature and comprises a bran fraction that contains the majority of lignocellulosic (bran) fibers. As an example, corn fiber is a heterogeneous complex of carbohydrate polymers and lignin. It is primarily composed of the outer kernel covering or seed pericarp, along with 10-25% adherent starch. Carbohydrate analyses of corn fiber vary considerably according to the source of the material. The lignocellulosic biomass may comprise hemicellulose.

In a preferred embodiment, the biomass hydrolysate is made by acid hydrolysis of C6 sugars, particularly fructose, glucose, or mixtures thereof. Sucrose ($C_{12}H_{22}O_{11}$) can be broken down into one molecule of glucose ($C_6H_{12}O_6$) plus one molecule of fructose (also $C_6H_{12}O_6$, an isomer of glucose), in a weakly acidic environment by a process called inversion. Fructose can also be made by enzymatic isomerization of glucose. Sucrose is commonly produced from biomass such as beet, corn and cane. Thus, within the context of the invention, glucose and fructose are biomass-derived.

The biomass hydrolysate is obtained by (preferably acid) hydrolysis under conditions such that it results in the formation of levulinic acid. Suitable acids for acid hydrolysis of biomass include sulphuric acid, hydrochloric acid, and phosphoric acid. A preferred acid is sulphuric acid, preferably diluted sulphuric acid, for example at a concentration between 1.5-3%. The temperature in the acid hydrolysis may depend on the source of carbohydrates, and may range between 100 and 250° C., 120 and 250° C., between 150-250° C., preferably between 170-240° C., more preferably between 190-230° C., even more preferably between 200 and 220° C. The acid hydrolysis may comprise one, two, or more stages. The pressure may also depend on the source of carbohydrates, as well as on the temperature, and may be anywhere between 1 and 50 bar, preferably between 5 and 40 bar, even more preferably between 10 and 30 bar. Suitable reactors include plugflow reactors, backmix reactors, and CSTR reactors. Different reactors for different stages may be used. Suitable reaction conditions for the acid hydrolysis of biomass or biomass-derived compounds are known in the art.

The concentration of levulinic acid in the biomass hydrolysate is preferably around 3.5 wt % based on the total weight of the biomass hydrolysate, for example it may be between 1 and 7 wt %, between 2 and 6 wt %, more preferably between 3 and 5 wt %.

In a further aspect the invention provides the use of the solvent as extraction solvent in the separation of levulinic acid from a biomass hydrolysate.

FIG. 1

Extraction coefficients of levulinic acid and formic acid in o-cresol, starting from a concentrated biomass hydrolysate containing 10.0 wt % levulinic acid (LA), 2.7 wt % formic acid (FA), 0.40 wt % acetic acid, and 10 wt % $H_2SO_4$.

FIG. 2

Extraction coefficients of levulinic acid and formic acid in 2.6 dimethylphenol starting from a concentrated biomass hydrolysate containing 10.0 wt % levulinic acid (LA), 2.7 wt % formic acid (FA), 0.40 wt % acetic acid, and 10 wt % $H_2SO_4$.

FIG. 3

Extraction coefficients of levulinic acid in m-cresol, starting from a synthetic mixture containing 8.6 wt % $H_2SO_4$, 10 wt % levulinic acid, 4 wt % formic acid, and starting from a biomass hydrolysate containing ≈9 wt % $H_2SO_4$, 8.8 wt % levulinic acid, 2.6 wt % formic acid, and 0.45 wt % acetic acid.

FIG. 4

Extraction coefficients of levulinic acid in m-cresol, starting from a synthetic mixture containing 8.6 wt % $H_2SO_4$, 10 wt % levulinic acid, 4 wt % formic acid, and starting from a biomass hydrolysate containing ≈9 wt % $H_2SO_4$, 8.8 wt % levulinic acid, 2.6 wt % formic acid, and 0.45 wt % acetic acid.

EXAMPLES

The extraction coefficient $K_{ext}$ is defined as wt % (LA) organic phase/wt % (LA) aqueous phase.

Example 1 o-Cresol and 2,6 Diethyl Phenol

Preparation of a Concentrated Biomass Hydrolysate

A biomass hydrolysate was prepared by acid hydrolysis of softwood. The biomass hydrolysate (500 g) was concentrated by evaporation using a Rota Vapor until 175 grams. The condensate of this evaporation was a clear colourless liquid. The composition of the concentrated biomass hydrolysate is summarized in Table 1.

TABLE 1

Composition of the concentrated biomass hydrolysate

| Component | Concentration (wt %) |
|---|---|
| $H_2SO_4$ | ≈10 |
| Levulinic acid | 10 |
| Formic acid | 2.7 |
| Acetic acid | 0.4 |

Extraction of the Concentrated Biomass Hydrolysate

To approximately 100 g of the concentrated biomass hydrolysate was added approximately 100 g of either o-cresol or 2,6 dimethyl phenol (2,6 DMP). The resulting biphasic systems were stirred at 60° C. (±1° C.) for approx. 30 minutes. After phase separation (approximately one hour) the aqueous phase and the organic phase were isolated and analyzed by HPLC. The results are summarized in Tables 2 and 3 (OP, organic phase).

Distillation of the Organic Phase

Based upon the composition of the organic phases obtained from o-cresol and 2,6 dimethyl phenol, synthetic solutions were made by adding levulinic acid, formic acid, and water to o-cresol and 2,6 DMP, respectively, to mimic the organic phases. These synthetic solutions were prepared in greater volumes, in order to be able to conduct distillation experiments, in order to predict the behaviour of the organic phases in subsequent distillation, see Table 4.

TABLE 4

Composition of synthetic solutions

| Component | Concentration in synthetic solution of o-cresol (wt %) | Concentration in synthetic solution of 2,6 DMP (wt %) |
|---|---|---|
| Levulinic acid | 26.7 | 15.3 |
| Formic acid | 1.7 | 1.5 |
| Water | 16.7 | 6.9 |
| Solvent | 55.0 | 76.3 |

The synthetic solutions were distilled over a small lab scale column (Dufton type distillation column, length=30 cm), without using reflux. The total distillate was collected in different fractions. The distillation was started at 200 mbar until the bottom temperature reached 150° C. At this point the distillation was interrupted to analyze the collected fractions. The distillation was continued at 20 mbar until the bottom temperature reached 150° C. Collected fractions and bottom product were analyzed. A concentrated stream of formic acid was obtained. Furthermore, no degradation of levulinic acid was observed. The balance over levulinic acid was closed, and no other components were detected.

mately 100 g of m-cresol. The resulting biphasic systems were stirred at 60° C. (±1° C.) for approximately 30 minutes. After phase separation (approximately one hour) the aqueous phase and the organic phase were isolated and analyzed by HPLC. The results are summarized in Tables 6 and 7.

TABLE 2

Extraction results obtained with o-cresol

| Levulinic acid | | | Formic acid | | | Acetic acid | | | $H_2O$ |
| --- | --- | --- | --- | --- | --- | --- | --- | --- | --- |
| aq phase wt % | org phase wt % | $K_{ext}$ | aq phase wt % | org phase wt % | $K_{ext}$ | aq phase wt % | org phase wt % | $K_{ext}$ | in OP wt % |
| 2.2 | 10.1 | 4.6 | 2.3 | 1.0 | 0.45 | 0.24 | 0.28 | 1.17 | 11.9 |
| 1.3 | 6.6 | 5.2 | 2.0 | 0.9 | 0.45 | 0.17 | 0.20 | 1.18 | 10.9 |
| 0.7 | 3.9 | 5.9 | 1.6 | 0.7 | 0.43 | 0.11 | 0.12 | 1.16 | 9.0 |

TABLE 3

Extraction results obtained with 2,6 DMP

| Levulinic acid | | | Formic acid | | | Acetic acid | | | $H_2O$ |
| --- | --- | --- | --- | --- | --- | --- | --- | --- | --- |
| aq phase wt % | org phase wt % | $K_{ext}$ | aq phase wt % | org phase wt % | $K_{ext}$ | aq phase wt % | org phase wt % | $K_{ext}$ | in OP wt % |
| 5.6 | 12.9 | 2.3 | 2.6 | 0.8 | 0.30 | 0.34 | 0.32 | 0.94 | 6.8 |
| 3.2 | 8.0 | 2.5 | 2.4 | 0.6 | 0.27 | 0.26 | 0.24 | 0.92 | 5.6 |
| 1.5 | 3.9 | 2.6 | 2.0 | 0.5 | 0.24 | 0.16 | 0.15 | 0.96 | 4.3 |

Comparative Example A m-Cresol

Preparation of a Concentrated Biomass Hydrolysate

A biomass hydrolysate was prepared by acid hydrolysis of softwood. The biomass hydrolysate (250 g) was concentrated by evaporation using a Rota Vapor until 100 grams. The condensate of this evaporation was a clear colorless liquid. In addition, a synthetic mixture was prepared containing levulinic acid, formic acid, and acetic acid, to mimic the concentrated biomass hydrolysate. The compositions of the concentrated biomass hydrolysate and the synthetic mixture are summarized in Table 5.

TABLE 5

Composition of the concentrated biomass hydrolysate & synthetic mixture

| Component | Synthetic mixture (wt %) | Concentrated biomass hydrolysate (wt %) |
| --- | --- | --- |
| $H_2SO_4$ | 8.6 | ≈9 |
| Levulinic acid | 10 | 8.8 |
| Formic acid | 4 | 2.6 |
| Acetic acid | Not added | 0.45 |

Extraction of the Concentrated Biomass Hydrolysate

To approximately 100 g of both concentrated biomass hydrolysate and the synthetic mixture was added approxi- Distillation of the Organic Phase Based upon the composition of the organic phase obtained from m-cresol, a synthetic solution was made by adding levulinic acid, formic acid, and water in m-cresol, to mimic said organic phase. This synthetic solution was prepared in greater volume, in order to be able to conduct distillation experiments, to predict the behaviour of the organic phase in a subsequent distillation step, see Table 8.

TABLE 6

Extraction data with synthetic mixture

| Levulinic acid | | | Formic acid | | | $H_2O$ |
| --- | --- | --- | --- | --- | --- | --- |
| aq phase wt % | org phase wt % | $K_{ext}$ | aq phase wt % | org phase wt % | $K_{ext}$ | in OP wt % |
| 6.05 | 16.3 | 2.7 | 3.80 | 1.82 | 0.48 | 20.5 |
| 3.77 | 11.9 | 3.2 | 3.69 | 1.61 | 0.44 | 17.4 |
| 1.77 | 6.7 | 3.8 | 3.10 | 1.31 | 0.42 | 14.8 |
| 0.58 | 2.4 | 4.1 | 2.92 | 1.08 | 0.37 | 13.7 |
| | 0 | | | | | 12.7 |

TABLE 7

Extraction data with concentrated biomass hydrolysate

| Levulinic acid | | | Formic acid | | | Acetic acid | | | H$_2$O |
|---|---|---|---|---|---|---|---|---|---|
| aq phase wt % | org phase wt % | K$_{ext}$ | aq phase wt % | org phase wt % | K$_{ext}$ | aq phase wt % | org phase wt % | K$_{ext}$ | in OP wt % |
| 4.20 | 13.7 | 3.3 | 2.39 | 1.30 | 0.54 | 0.35 | 0.40 | 1.14 | 17.3 |
| 2.30 | 9.4 | 4.1 | 2.12 | 1.10 | 0.52 | 0.24 | 0.28 | 1.17 | 15.3 |
| 1.31 | 5.8 | 4.4 | 1.95 | 0.89 | 0.46 | 0.20 | 0.23 | 1.15 | 13.2 |
| 0.35 | 1.7 | 5.0 | 1.73 | 0.73 | 0.42 | 0.13 | 0.16 | 1.23 | 12.8 |
| | 0 | | | | | | | | 12.6 |

TABLE 8

Composition synthetic solution

| Component | Concentration in the synthetic solution (wt %) |
|---|---|
| Levulinic acid | 20 |
| Formic acid | 2.5 |
| Water | 20 |
| Solvent | 57.5 |

The solution was distilled over a small lab scale column (Dufton type distillation column, length=30 cm), without using reflux. The total distillate was collected in different fractions. The distillation was started at 200 mbar until the bottom temperature reached 150° C. Three fractions were collected. The third fraction 3 contained 42 wt % formic acid and 58 wt % water. The total distillation time was around 1 hour. The bottom was kept at 150° C. and the heat input was regulated such that the top temperature did not increase above 110° C. This condition was maintained for an additional hour, resulting in a small fraction consisting mainly of water and m-cresol. At this stage, about 33% of the initial levulinic acid was lost. The distillation was continued at a pressure of 20 mbar to remove the m-cresol. At the end of the distillation, 85% of the m-cresol could be recovered. Analysis of the bottom product showed a further decrease of levulinic acid. The overall loss levulinic acid was approximately 54%. NMR analysis showed the presence of a cresol ester of levulinic acid, which may explain the cause for the loss of levulinic acid and m-cresol.

Comparative Example B

Higher Alkyl Groups

Using the same procedure as in Example 1, levulinic acid was extracted from a biomass hydrolysate containing 0.17 wt % glucose, 0.08 wt % xylose, 0.64 wt % formic acid, 0.14 wt % acetic acid, 1.76 wt % levulinic acid, and 0.02 wt % furfural, using solvents as listed in Table 9. The extraction efficiency is expressed as the extraction coefficient.

TABLE 9

Extraction coefficients for levulinic acid

| Extraction solvent | Extraction coefficient |
|---|---|
| phenol | 4.0 |
| 2-tert butylphenol | 1.2 |
| 2-sec butylphenol | 0.94 |
| 4- tert octylphenol | 0.85 |
| 2,4 di-tert butylphenol | 0.6 |

The higher alkylphenols (2-tert butylphenol, 2-sec butylphenol, 4-tert octylphenol, 2,4 di-tert butylphenol) give very poor extraction efficiency. The organic phase obtained with phenol can be subjected to a subsequent distillation, but this will result in the formation of levulinic-phenol esters, which makes it an unsuitable extraction solvent for levulinic acid. Moreover, the mutual solubility with phenol is poor.

Example 2

2-Propylphenol and Guaiacol

A synthetic biomass hydrolysate was made to have the concentrations stated in Table 10. To approximately 25 mL of this synthetic biomass hydrolysate was added approximately 25 mL of either 2-proplphenol or guaiacol. The resulting biphasic systems were shaken at 60° C. (±1° C.) for approx. 2 h. After phase separation the aqueous phase and the organic phase were isolated, weight and the aqueous phase (AP) was analyzed by HPLC. The organic phase (OP) was analysed by Karl-Fischer titration for its water content. The results are summarized in Table 11.

TABLE 10 synthetic biomass hydrolysate

| Substance | concentration |
|---|---|
| Levulinic acid | 9.0 wt % |
| Formic acid | 0.98 wt % |
| Acetic acid | 0.45 wt % |
| Furfural | 0.09 wt % |
| Sulphuric acid | 9.0 wt % |

TABLE 11

Extraction results obtained with 2-propylphenol and guaiacol

| | 2-propylphenol K$_{ext}$ | Guaiacol K$_{ext}$ |
|---|---|---|
| Levulinic acid | 2.83 | 1.46 |
| formic acid | 0.03 | 0.17 |
| Acetic acid | 0.46 | 0.44 |
| Solvent in AP | 0.32 | 2.00 |
| Water in OP | 5.70 | 6.00 |

Example 3

A Mixture of Guaiacol and 2-Methylresorcinol

A synthetic biomass hydrolysate was made to have the concentrations stated in Table 10. To approximately 25 mL of the synthetic biomass hydrolysate (composition please see Table 4 example 2) was added approximately 25 mL of a 50/50 mixture of guaiacol and 2-methylresorcinol. The resulting biphasic systems were shaken at 60° C. (±1° C.) for approx. 2 h. After phase separation the aqueous phase and the organic phase were isolated, weight and the aqueous phase (AP) was analyzed by HPLC. The organic phase (OP) was analysed by Karl-Fischer titration for its water content. The results are summarized in Table 12.

TABLE 12

Extraction results obtained with 2-propylphenol and guaiacol

| | Mixture guaiacol/2-methylresorcinol $K_{ext}$ |
|---|---|
| Levulinic acid | 1.91 |
| formic acid | 0.18 |
| Acetic acid | 0.43 |
| Solvent in AP | 1.90/1.70 |
| Water in OP | 8.90 |

The invention claimed is:

1. A process for separating levulinic acid from a biomass hydrolysate said process comprising extracting the levulinic acid from the biomass hydrolysate using as an organic solvent a substituted benzene comprising:

(i) at least one $OR_1$ group wherein $R_1$ is H or $CH_3$; and (ii) at least one $C_{1-3}$ alkyl group, wherein each of the at least one $OR_1$ group is ortho positioned to at least one $C_{1-3}$ alkyl group.

2. The process according to claim 1, wherein the substituted benzene is selected from the group consisting of compounds I to VI:

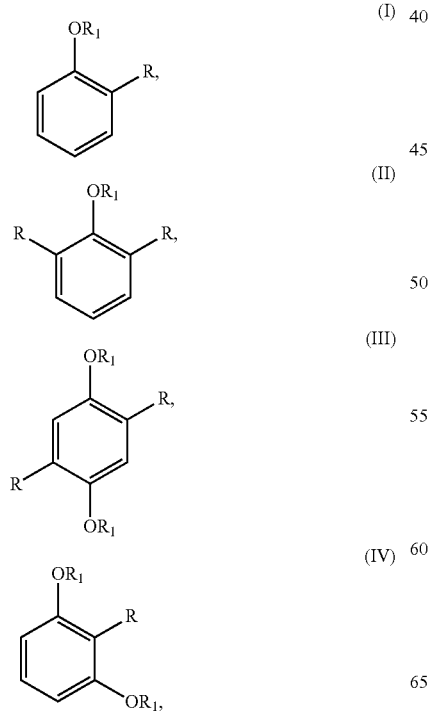

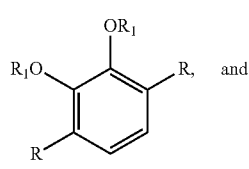

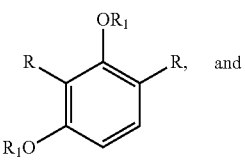

wherein R represents a $C_{1-3}$ alkyl group.

3. The process according to claim 1, wherein the $C_{1-3}$ alkyl group is a methyl group.

4. The process according to claim 1, wherein the substituted benzene is ortho-cresol, 2,6 dimethylphenol, or a mixture thereof.

5. The process according to claim 1, wherein the extraction is carried out at a temperature of between 50° C. to 80° C.

6. The process according to claim 1, wherein prior to the extraction, the biomass hydrolysate is subjected to solid-liquid separation.

7. The process according to claim wherein a recovered organic phase is subjected to distillation.

8. A process for separating levulinic acid from a biomass hydrolysate, comprising:

contacting the biomass hydrolysate with a solvent to produce an aqueous phase and an organic phase comprising the levulinic acid and the solvent, wherein the solvent comprises a substituted benzene comprising at least one $OR_1$ group and at least one $C_{1-3}$ alkyl group, wherein $R_1$ is H or $CH_3$, and wherein each $OR_1$ group is ortho positioned relative to at least one $C_{1-3}$ alkyl group; and separating the organic phase from the aqueous phase.

9. The process of claim 8, wherein the biomass hydrolysate is at a temperature of 50° C. to 80° C. when the organic phase is separated from the aqueous phase.

10. The process of claim 8, wherein the solvent comprises ortho-cresol, 2,6 dimethylphenol, or a mixture thereof.

11. The process of claim 8, wherein the levulinic acid is separated from the organic phase by distillation.

12. The process of claim 8, wherein the $C_{1-3}$ alkyl group comprises a methyl group, an ethyl group, a propyl group, or an isopropyl group.

13. The process of claim 8, wherein the biomass hydrolysate comprises 1 wt % to 7 wt % of the levulinic acid.

14. The process of claim 8, wherein the biomass hydrolysate further comprises formic acid and sulphuric acid.

15. The process of claim 8, wherein the substituted benzene comprises a compound having a formula:

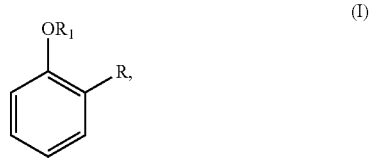

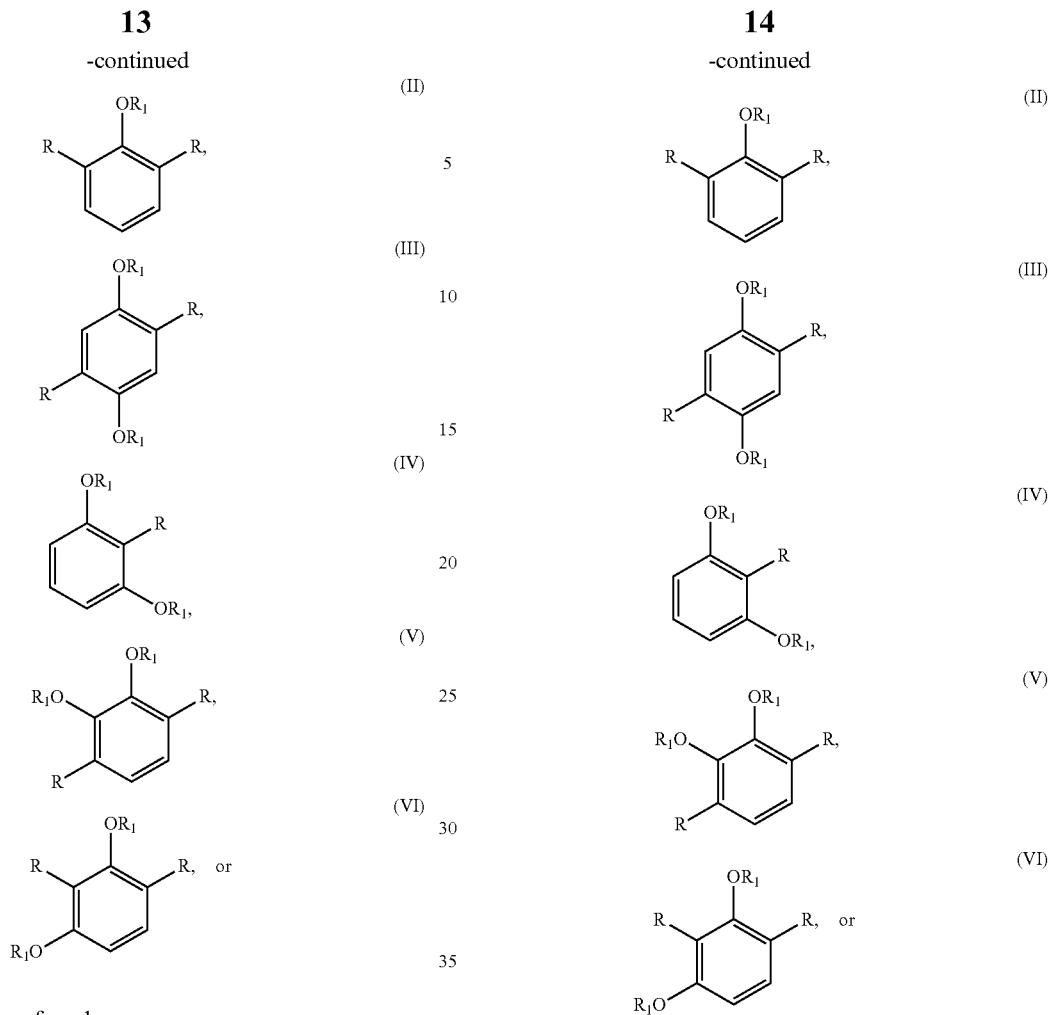

a mixture thereof, and
wherein R represents a $C_{1-3}$ alkyl group.

16. A process for separating levulinic acid from a biomass hydrolysate, comprising:
   contacting the biomass hydrolysate with a solvent to produce an aqueous phase and an organic phase comprising the levulinic acid and the solvent, wherein the biomass hydrolysate is at a temperature of about 50° C. to about 80° C., wherein the solvent comprises a substituted benzene comprising at least one $OR_1$ group and at least one $C_{1-3}$ alkyl group, wherein $R_1$ is H or $CH_3$, and wherein each $OR_1$ group is ortho positioned relative to at least one $C_{1-3}$ alkyl group;
   separating the organic phase from the aqueous phase; and
   separating the levulinic acid from the organic phase.

17. The process of claim 16, wherein the levulinic acid is separated from the organic phase by distillation.

18. The process of claim 16, wherein the biomass hydrolysate comprises 1 wt % to 7 wt % of the levulinic acid.

19. The process of claim 16, wherein the substituted benzene comprises a compound having a formula:

a mixture thereof, and
wherein R represents a $C_{1-3}$ alkyl group.

20. The process of claim 16, wherein:
prior to contacting the biomass hydrolysate with the solvent, the biomass hydrolysate is subjected to solid-liquid separation,
the levulinic acid is separated from the organic phase by distillation, and
the substituted benzene comprises a compound having a formula:

-continued
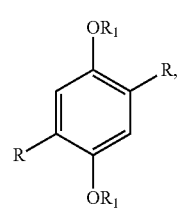
(III)
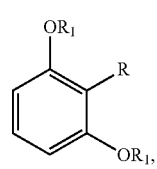
(IV)
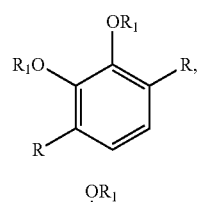
(V)
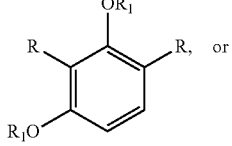
(VI)
or
a mixture thereof, and wherein R represents a $C_{1-3}$ alkyl group.
* * * * *